(12) United States Patent
Selkee

(10) Patent No.: US 9,861,790 B2
(45) Date of Patent: *Jan. 9, 2018

(54) STEERING MECHANISM FOR BI-DIRECTIONAL CATHETER

(71) Applicant: BIOSENSE WEBSTER, INC., Diamond Bar, CA (US)

(72) Inventor: Thomas V. Selkee, Claremont, CA (US)

(73) Assignee: BIOSENSE WEBSTER, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/331,671

(22) Filed: Oct. 21, 2016

(65) Prior Publication Data

US 2017/0035994 A1 Feb. 9, 2017

Related U.S. Application Data

(63) Continuation of application No. 14/608,118, filed on Jan. 28, 2015, now Pat. No. 9,474,879, which is a
(Continued)

(51) Int. Cl.
*A61M 25/01* (2006.01)
*A61M 25/00* (2006.01)

(52) U.S. Cl.
CPC ...... *A61M 25/0147* (2013.01); *A61M 25/005* (2013.01); *A61M 25/0082* (2013.01); *A61M 25/0136* (2013.01)

(58) Field of Classification Search
CPC ................ A61M 25/0136; A61M 25/0147
See application file for complete search history.

(56) References Cited

U.S. PATENT DOCUMENTS 5,273,535 A 12/1993 Edwards et al.
RE34,502 E 1/1994 Webster, Jr.
(Continued)

FOREIGN PATENT DOCUMENTS

JP 09-075301 3/1997
JP 2000-197642 A 7/2000

OTHER PUBLICATIONS

European Patent Search Report dated Sep. 19, 2005 for corresponding International Application No. EP 05 25 3690, in the name of Biosense Webster, Inc.
(Continued)

*Primary Examiner* — Laura Bouchelle
(74) *Attorney, Agent, or Firm* — Lewis Roca Rothgerber Christie LLP

(57) ABSTRACT

The present invention provides a bi-directional catheter with nearly double the throw in its catheter tip deflection. In particular, the travel path of each the puller wire includes a U-turn or doubling-back around a pulley which minimizes the offset angle between the puller wire and the longitudinal axis of the control handle while maximizing the travel distance of that puller wire for any given distance traveled by the pulley drawing the puller wire. In one embodiment, the catheter has an elongated catheter body, a catheter tip section with first and second diametrically-opposed off-axis lumens, and a control handle which includes a steering assembly having a lever structure carrying a pair of pulleys for simultaneously drawing and releasing corresponding puller wires to deflect the tip section of the catheter.

20 Claims, 12 Drawing Sheets

Related U.S. Application Data continuation of application No. 13/719,143, filed on Dec. 18, 2012, now Pat. No. 8,956,322, which is a continuation of application No. 12/127,704, filed on May 27, 2008, now Pat. No. 8,348,888, which is a continuation of application No. 10/871,691, filed on Jun. 15, 2004, now Pat. No. 7,377,906.

(56) References Cited

U.S. PATENT DOCUMENTS

| | | |
|---|---|---|
| 5,358,478 A | 10/1994 | Thompson et al. |
| 5,395,327 A | 3/1995 | Lundquist et al. |
| 5,395,328 A | 3/1995 | Ockuly et al. |
| 5,456,664 A | 10/1995 | Heinzelman et al. |
| 5,531,686 A | 7/1996 | Lundquist et al. |
| 5,562,619 A | 10/1996 | Mirarchi et al. |
| 5,571,085 A | 11/1996 | Accisano, III |
| 5,626,553 A | 5/1997 | Frassica et al. |
| 5,676,653 A | 10/1997 | Taylor et al. |
| 5,741,320 A | 4/1998 | Thornton et al. |
| 5,891,088 A | 4/1999 | Thompson et al. |
| 5,944,690 A | 8/1999 | Falwell et al. |
| 6,033,378 A | 3/2000 | Lundquist et al. |
| 6,171,277 B1 | 1/2001 | Ponzi |
| 6,198,974 B1 | 3/2001 | Webster, Jr. |
| 6,210,407 B1 | 4/2001 | Webster |
| 6,485,455 B1 | 11/2002 | Thompson et al. |
| 6,530,897 B2 | 3/2003 | Nardeo |
| 6,579,278 B1 | 6/2003 | Bencini |
| 6,648,875 B2 | 11/2003 | Simpson et al. |
| 7,377,906 B2 | 5/2008 | Selkee |
| 7,591,799 B2 | 9/2009 | Selkee |
| 9,474,879 B2 * | 10/2016 | Selkee .............. A61M 25/0136 |
| 2002/0165484 A1 | 11/2002 | Bowe et al. |
| 2004/0143197 A1 | 7/2004 | Soukup et al. |

OTHER PUBLICATIONS

English translation of JP Office action dated Aug. 3, 2010 in JP Application No. 2005-173994, 3 pages.

\* cited by examiner

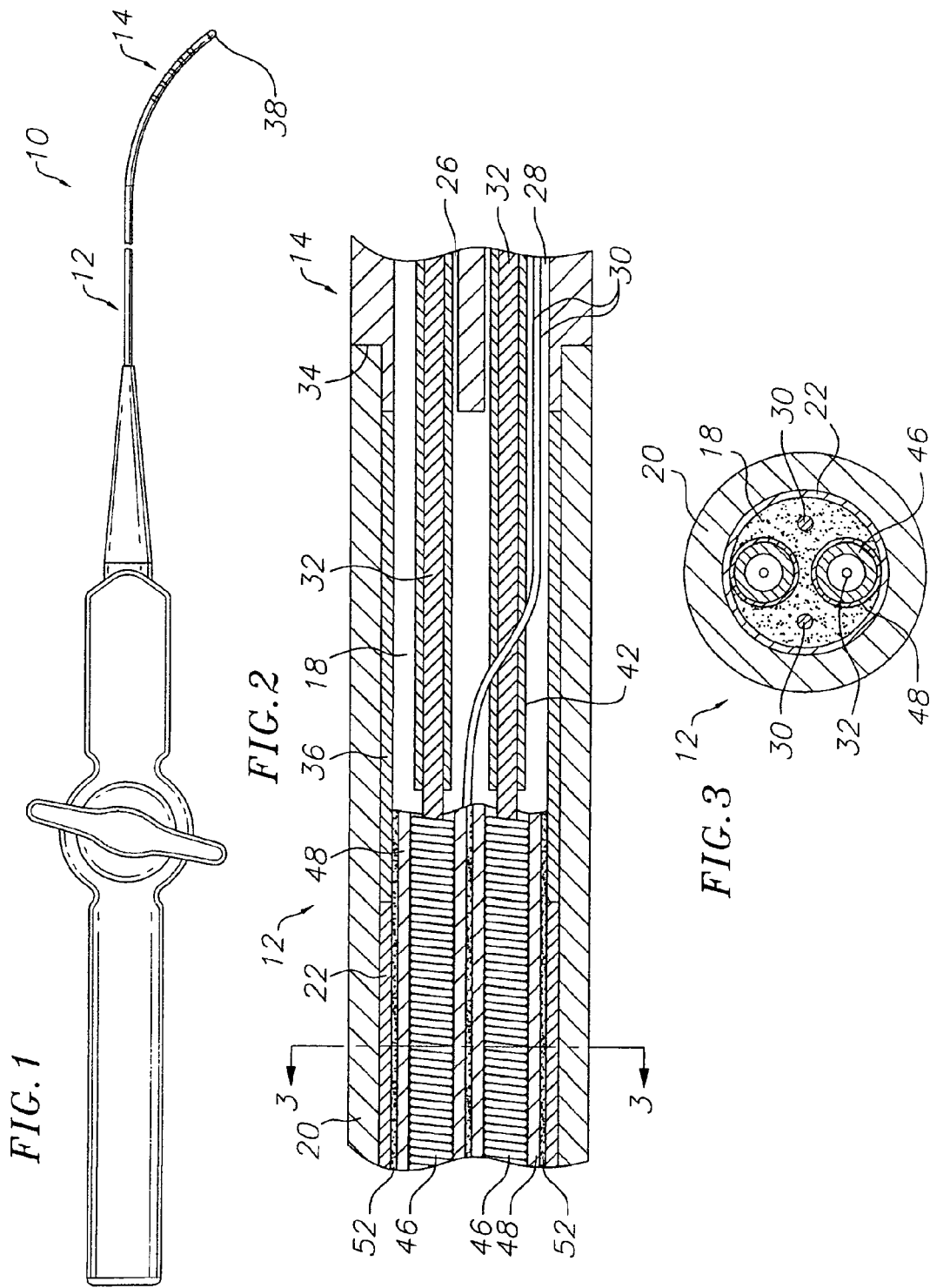

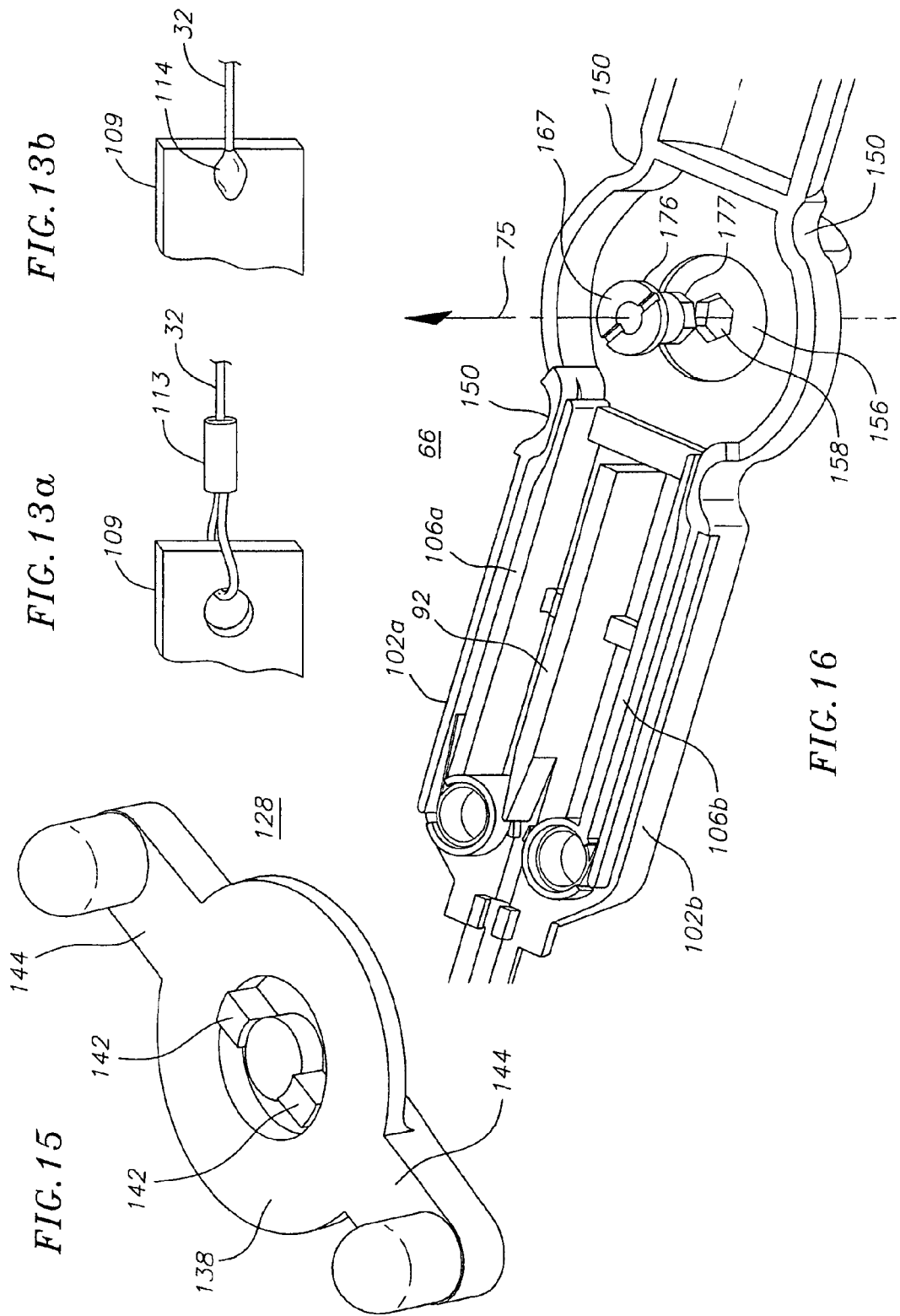

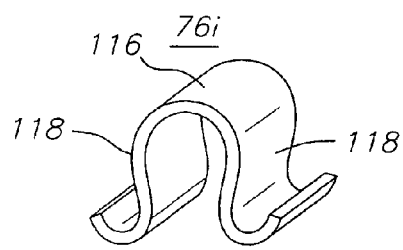
FIG.14a
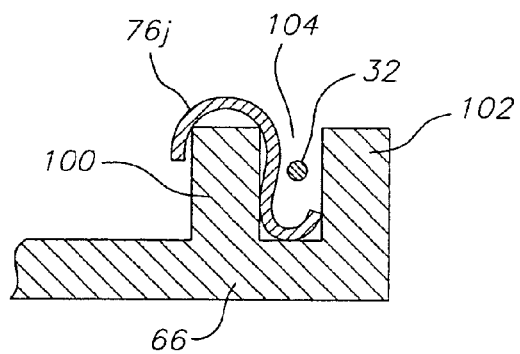
FIG.14d
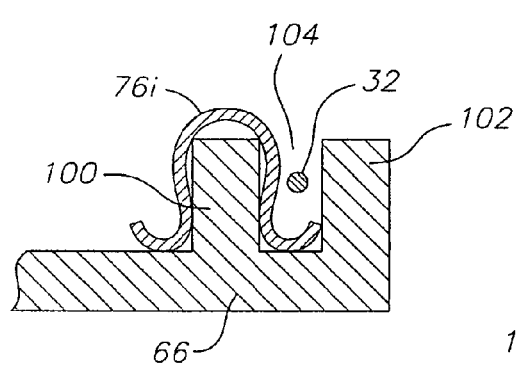
FIG.14b
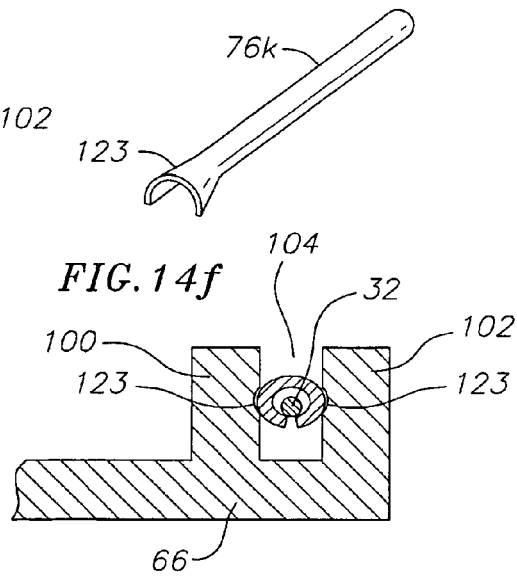
FIG.14e
FIG.14f
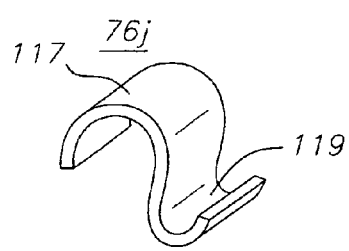
FIG.14c
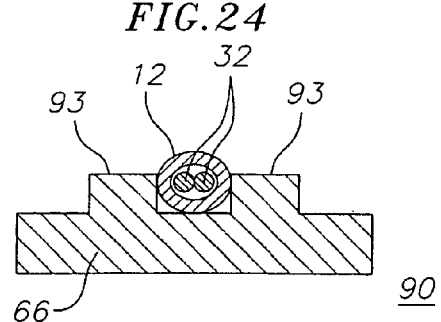
FIG.24

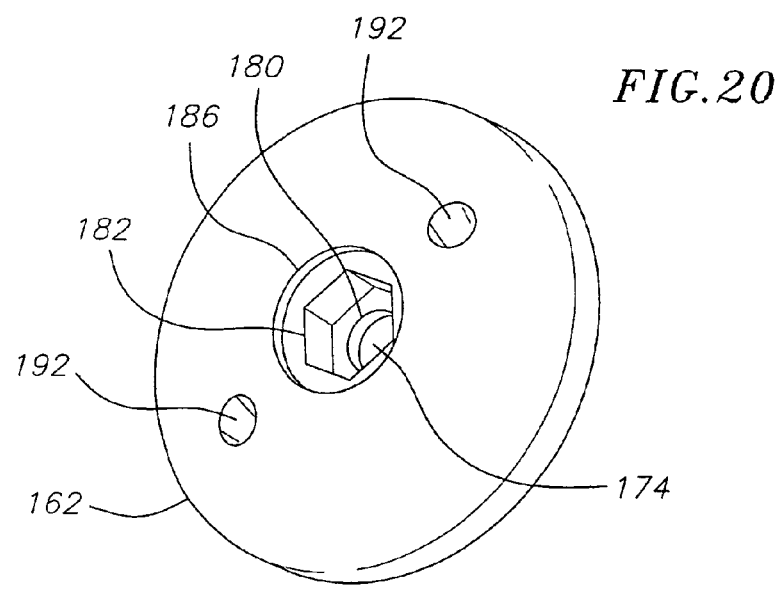
FIG.20
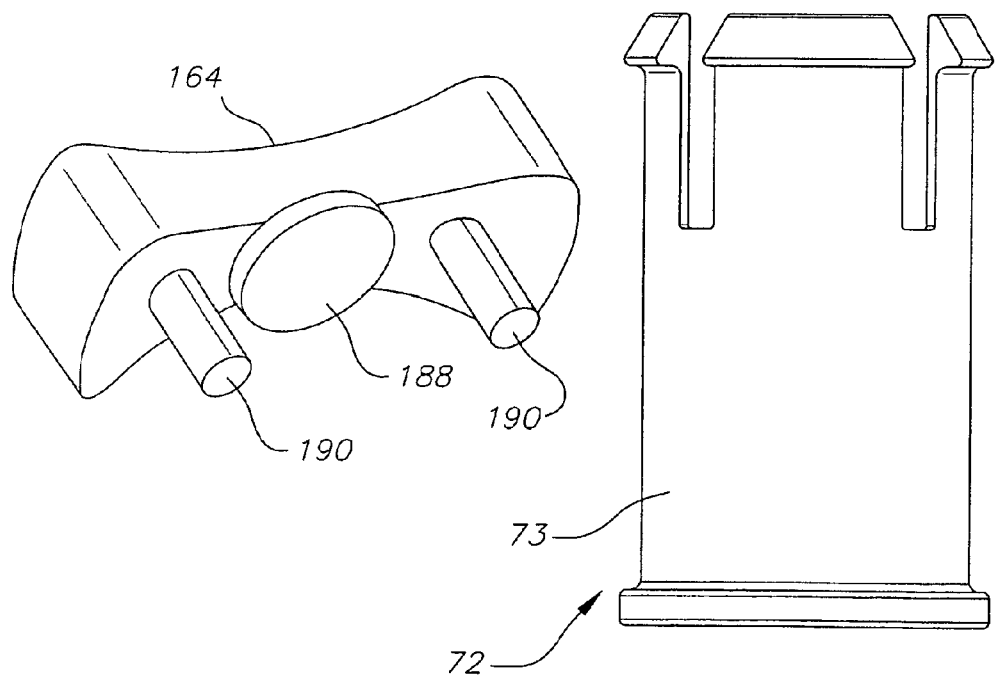
FIG.21
FIG.22

STEERING MECHANISM FOR BI-DIRECTIONAL CATHETER

CROSS-REFERENCE TO RELATED APPLICATION(S)

This application is a continuation of, and claims priority to and the benefit of, U.S. application Ser. No. 14/608,118 filed Jan. 28, 2015, issued as U.S. Pat. No. 9,474,879, which is a continuation of U.S. application Ser. No. 13/719,143 filed Dec. 18, 2012, issued as U.S. Pat. No. 8,956,322, which is a continuation of U.S. application Ser. No. 12/127,704 filed May 27, 2008, issued as U.S. Pat. No. 8,348,888, which is a continuation of U.S. application Ser. No. 10/871,691 filed Jun. 15, 2004, issued as U.S. Pat. No. 7,377,906, the entire contents of all of which are incorporated herein by reference.

FIELD OF THE INVENTION

The present invention relates to improved bidirectional steerable catheters, and more particularly to a catheter having a bidirectional control handle.

BACKGROUND OF THE INVENTION

Electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart which is of concern. Within the heart, the ability to control the exact position and orientation of the catheter tip is critical and largely determines how useful the catheter is.

Bidirectional catheters have been designed to be deflectable in one direction by one puller wire and in the opposite direction within the same plane by a second puller wire. In such a construction, the puller wires extend into opposing off-axis lumens within the tip section of the catheter. So that the tip section can bend in both directions in the same plane, the puller wires and their associated lumens must be located along a diameter of the tip section. For ablation catheters, electrode lead wires must also be provided within the distal end. Typically, an additional lumen is used to contain the electrode lead wires. For example, U.S. Pat. No. 6,210,407, the disclosure of which is incorporated herein by reference, is directed to a bi-directional catheter comprising two puller wires and a control handle having at least two moveable members longitudinally movable between first and second positions. The proximal end of each puller wire is connected to an associated movable member of the control handle. Proximal movement of a movable member relative to the catheter body results in proximal movement of the puller wire associated with that movable member relative to the catheter body, and thus deflection of the tip section in the direction of the lumen in which that puller wire extends.

As another example, U.S. Pat. No. 6,171,277, the disclosure of which is incorporated herein by reference, is directed to a bidirectional steerable catheter having a control handle that houses a generally-circular spur gear and a pair of spaced apart rack gears. Each rack gear is longitudinally movable between first and second positions, whereby proximal movement of one rack gear results in rotational movement of the spur gear, and correspondingly distal movement of the other rack gear. Two puller wires extend from the control handle whose the distal ends are fixedly attached to the tip section, and whose proximal ends are each anchored to a separate associated rack gear in the control handle. Proximal movement of a rack gear and its associated puller wire relative to the catheter body results in deflection of the tip section in the direction of the off axis lumen into which that puller wire extends.

Also known is U.S. Pat. No. 6,198,974, the disclosure of which is incorporated herein reference, is directed to a bi-directional electrode catheter comprising a control handle. At their proximal ends, two pairs of puller wires are attached to movable pistons in the control handle. Each piston is controlled by an operator using a slidable button fixedly attached to each piston. Movement of selected buttons results in deflection of the tip section into a generally planar "U"- or "S"-shaped curve.

Further known is U.S. Pat. No. 5,891,088, the disclosure of which is incorporated, directed to a steering assembly with asymmetric left and right curve configurations. Proximal ends of left and right steering wires are adjustably attached to a rotatable cam housed in a control handle. The rotatable cam has first and second cam surfaces which may be configured differently from each other to accomplish asymmetric steering.

While the aforementioned catheters provide bi-directional steering, the mechanical efficiencies of the steering or deflection mechanism can be improved upon. Because the control handle has limited interior space in which to house the steering mechanism, a need exists for a compact yet mechanically-efficient design to accomplish bi-directional steering. Moreover, a greater degree of deflection in the catheter tip is also desirable, particularly if it can be accomplished without requiring greater exertion on the part of the user. The steering assembly of aforementioned U.S. Pat. No. 5,891,088 employs a configuration whereby the puller wires extend to the cam surfaces of the rotatable cam at a greater than generally desirable angle from the longitudinal axis of the catheter shaft, which decreases the efficiency of the steering lever and increases friction losses in the operation of the steering assembly. In addition, the steering assembly therein generally limits the amount of longitudinal movement of the puller wires for deflecting the catheter tip to only the circumference of the rotatable cam. An improved catheter with bi-directional deflection is therefore desired.

SUMMARY OF THE INVENTION

The present invention provides a bi-directional catheter with nearly double the throw in its catheter tip deflection. In particular, the travel path of each the puller wire includes a U-turn or doubling-back around a pulley which minimizes the offset angle between the puller wire and the longitudinal axis of the control handle while maximizing the travel distance of that puller wire for any given distance traveled by the pulley drawing the puller wire.

In one embodiment, the catheter has an elongated catheter body, a catheter tip section with first and second diametrically-opposed off-axis lumens, and a control handle which includes a steering assembly having a lever structure carrying a pair of pulleys for simultaneously drawing and releasing corresponding puller wires to deflect the tip section of the catheter. In particular, the pulleys are rotatably mounted on opposing portions of the lever structure such that one pulley is moved distally as the other pulley is moved proximally when the lever structure is rotated. Because each puller wire is trained on a respective pulley, rotation of the lever structure causes the pulley that is moved proximally to draw its puller wire to deflect the tip section in the direction of the off-axis lumen in which that puller wire extends.

In a detailed embodiment of the invention, each puller wire is trained about its respective pulley for about 180-187 degrees. Moreover, each puller wire may extend from the distal end of the control handle to its respective pulley at an angle no greater than about 10 degrees, or more preferably between 7 and 8 degrees, from the longitudinal axis of the control handle. Furthermore, the range of rotation of the lever structure in deflecting the catheter tip can be predetermined through a predetermined profile or curvature in the housing of the control handle.

In another embodiment of the invention, the control handle of the catheter includes a pair of constant force springs to draw up slack in a released puller wire when the tip is deflected. The catheter may also include a pair of adjustable stops that are configured to stop the proximal ends of the puller wires from proximal movement beyond a predetermined stop location along the longitudinal axis. Fine, if not nearly infinitesimal, adjustment in the operating position of the puller wires is accomplished by selectively adjusting the placement of the stops distally or proximally within the catheter housing.

In another embodiment, the control handle of the catheter includes a deflection knob that is rotationally coupled to the lever structure which enables the user to control deflection of the tip section with, preferably, a thumb and an index finger, when grasping the control handle. The catheter may also include a tension adjustment mechanism for adjusting the tightness of the deflection knob. In one embodiment, the adjustment mechanism includes a cap and a dial rotationally coupled to each other, a friction nut, and a screw rotationally coupled to cap, whereby rotation of the dial selectively increases or decreases the frictional bearing on the lever structure.

In yet another embodiment, the control handle of the catheter is operational for deflection of the tip section without both housing halves of the control handle being joined together. In that regard, the steering assembly is configured to be operational when assembled within one housing half not yet joined with the other housing half. A port formation enables the catheter body to be releasably held in the one housing half such that the puller wires extending from the catheter body can be manipulated by the steering assembly so assembled.

BRIEF DESCRIPTION OF THE DRAWINGS

These and other features and advantages of the present invention will be better understood by reference to the following detailed description when considered in conjunction with the accompanying drawings wherein:

FIG. 1 is a side view of an embodiment of the catheter of the invention.

FIG. 2 is a side cross-sectional view of the junction of the catheter body and tip section of an embodiment of a catheter according to the invention.

FIG. 3 is a transverse cross-sectional view of the catheter body shown in FIG. 2 taken along line 3-3.

FIGS. 13a and 13b are views of different embodiments of a fastener fastening a free end of an embodiment of a constant force spring to a proximal end of a puller wire.

FIGS. 14a, 14c and 14e are perspective views of different embodiments of a stop member.

FIGS. 14b, 14d and 14f are cross-sectional views of the stop members of FIGS. 14a, 14c and 14e, respectively, as situated in a housing half of the control handle.

FIG. 15 is a view of a deflection knob.

FIG. 16 is a view of the housing half of FIG. 10 with parts broken away and a friction nut.

FIG. 20 is a view of a cap of the tension adjustment assembly.

FIG. 21 is a view of a finger dial of the tension adjustment assembly.

FIG. 22 is a view of a pulley.

FIG. 23 is a view of an embodiment of another housing half of the control handle.

FIG. 24 is a cross sectional view taken along Lines W-W in FIG. 10.

DETAILED DESCRIPTION OF THE INVENTION

Figure 4:
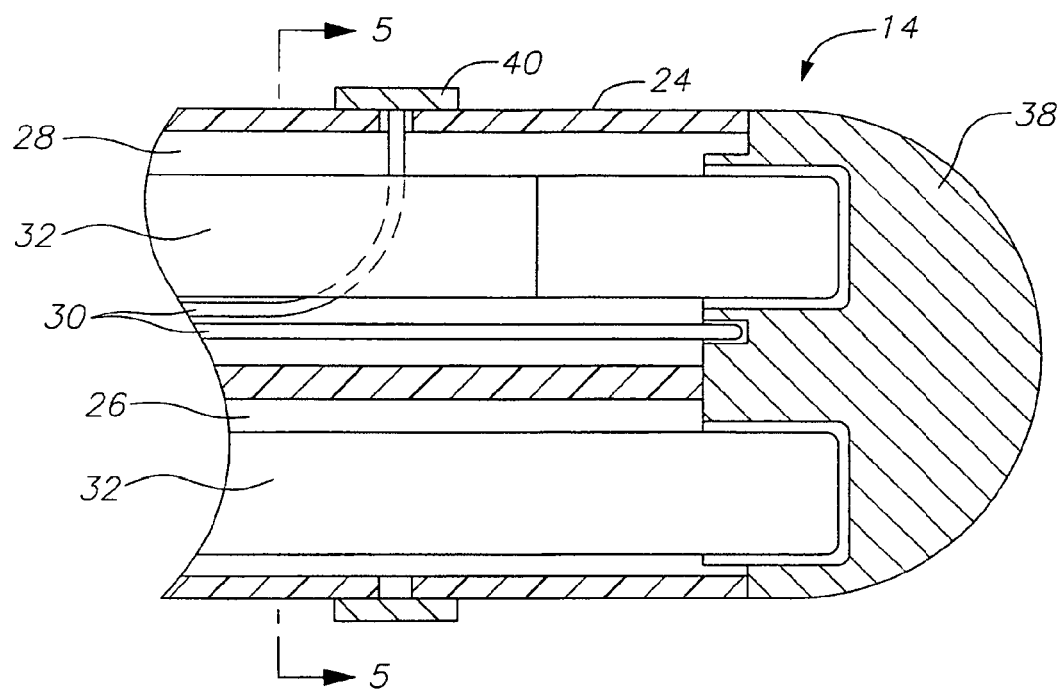
FIG. 4 is a side cross-sectional view of the distal end of the tip section shown in FIG. 2.

In an embodiment of the invention, there is provided a steerable bidirectional electrode catheter. As shown in FIG. 1, the catheter 10 comprises an elongated catheter body 12 having proximal and distal ends, a tip section 14 at the distal end of the catheter body 12, and a control handle 16 at the proximal end of the catheter body 12.

As shown in FIGS. 2 and 3, the catheter body 12 comprises an elongated tubular construction having a single axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 preferably comprises an imbedded braided mesh of stainless steel or the like to increase torsional stiffness of the catheter body 12 so that when the control handle 16 is rotated the tip section 14 will rotate in a corresponding manner.

The overall length and diameter of the catheter 10 may vary according to the application. A presently preferred catheter 10 has an overall length of about 48 inches. The outer diameter of the catheter body 12 is not critical, but is preferably no more than about 8 french. The inner surface of the outer wall 20 is preferably lined with a stiffening tube 22, which can be made of any suitable material, preferably nylon or polyimide. The stiffening tube 22, along with the braided outer wall 20, provides improved flexural and torsional stability while at the same time minimizing the wall thickness of the catheter body 12, thus maximizing the diameter of the central lumen 18. The outer diameter of the stiffening tube 22 is about the same as or slightly smaller than the inner diameter of the outer wall 20. A particularly preferred catheter 10 has an outer diameter of about 0.092 inch and a lumen 18 diameter of about 0.052 inch.

Figure 5:
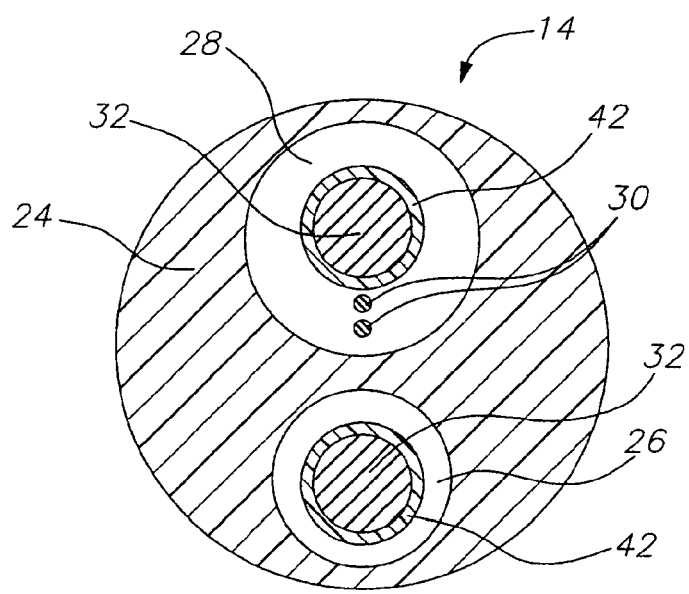
FIG. 5 is a transverse cross-sectional view of the tip section along line 5-5.
Figure 6:
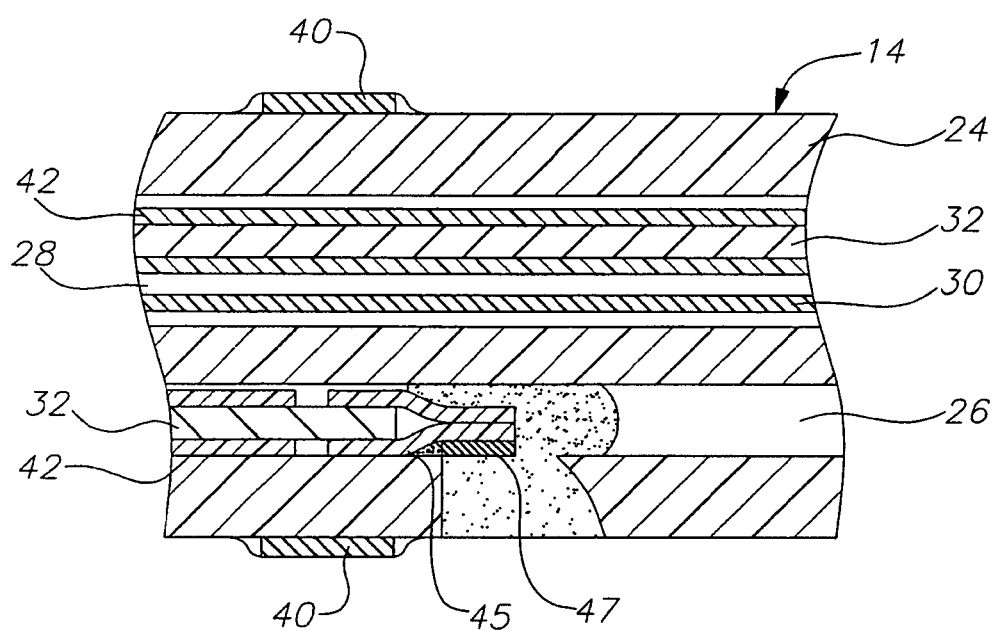
FIG. 6 is a transverse cross-sectional view of a catheter tip section according to the invention where the puller wires are anchored to the side walls of the tip section.

As shown in FIGS. 4 and 5, the tip section 14 comprises a short section of flexible tubing 24 having a first off-axis lumen 26 and a second off-axis lumen 28. The flexible tubing 24 is made of a suitable non-toxic material that is preferably more flexible than the catheter body 20. A presently preferred material for the tubing 24 is braided polyurethane, i.e., polyurethane with an embedded mesh of braided stainless steel or the like. The outer diameter of the tip section 14, like that of the catheter body 12, is preferably no greater than about 7 french, more preferably about 6½ french or less.

The off-axis lumens 26, 28 extend through diametrically opposed halves of the tip section 14. The off-axis lumens 26, 28 are asymmetrical and therefore non-interchangeable. The first off-axis lumen 26 is smaller than the second off-axis lumen 28. In an 8 french or 7 french diameter catheter, where the tip section is 6½ french, it is preferred that the first off-axis lumen 26 has a diameter ranging from about 0.018 inch to about 0.025 inch, more preferably from about 0.018 inch to about 0.022 inch. Preferably, the second off-axis lumen 28 has a diameter ranging from about 0.022 inch to about 0.030 inch, more preferably from about 0.026 inch to about 0.028 inch.

By using two rather than three lumens along a single diameter, the present design retains the simplified construction of the unidirectional deflectable steerable catheter described in U.S. Pat. No. Re 34,502, which is incorporated herein by reference. However, it is understood that additional lumens may be provided in the tip section. As described in U.S. Pat. No. 6,171,277, the disclosure of which is incorporated herein by reference, the tip section 14 may contain four lumens, two of which have a greater diameter of about 0.029 inch and two of which have a lesser diameter of about 0.018 inch. Lead wires for the electrodes, thermocouple wires and/or electromagnetic sensor cable may extend through different lumen(s) from those through which each of puller wires extends. As such, the present invention may employ two or more lumens in the tip section 14.

A preferred means for attaching the catheter body 12 to the tip section 14 is illustrated in FIG. 2. The proximal end of the tip section 14 comprises an outer circumferential notch 34 that receives the inner surface of the outer wall 20 of the catheter body 12. The tip section 14 and catheter body 12 are attached by glue or the like. Before the tip section 14 and catheter body 12 are attached, however, the stiffening tube 22 is inserted into the catheter body 12. The distal end of the stiffening tube 22 is fixedly attached near the distal end of the catheter body 12 by forming a glue joint with polyurethane glue or the like. Preferably a small distance, e.g., about 3 mm, is provided between the distal end of the catheter body 12 and the distal end of the stiffening tube 22 to permit room for the catheter body 12 to receive the notch 34 of the tip section 14. A force is applied to the proximal end of the stiffening tube 22, and, while the stiffening tube 22 is under compression, a first glue joint (not shown) is made between the stiffening tube 22 and the outer wall 20 by a fast drying glue, e.g. Super Glue®. Thereafter a second glue joint is formed between the proximal ends of the stiffening tube 22 and outer wall 20 using a slower drying but stronger glue, e.g., polyurethane.

A spacer 36 lies within the catheter body 12 between the distal end of the stiffening tube 22 and the proximal end of the tip section 14. The spacer 36 is preferably made of a material that is stiffer than the material of the tip section 14, e.g., polyurethane, but not as stiff as the material of the stiffening tube 22, e.g. polyimide. A spacer made of Teflon® is presently preferred. A preferred spacer 36 has a length of from about 0.25 inch to about 0.75 inch, more preferably about 0.50 inch. Preferably the spacer 36 has an outer and inner diameter about the same as the outer and inner diameters of the stiffening tube 22. The spacer 36 provides a transition in flexibility at the junction of the catheter body 12 and the tip section 14 to bend smoothly without folding or kinking.

In the depicted embodiment, the distal end of the tip section 14 carries a tip electrode 38 (see FIGS. 1 and 4). Mounted along the length of the tip section 14 is a ring electrode 40 (see FIG. 4). The length of the ring electrode 40 is not critical, but is preferably about 1 mm to about 3 mm. Additional ring electrodes can be provided if desired. If multiple ring electrodes are used, they are spaced apart in any fashion as desired so long as their edges do not touch.

As shown in FIGS. 2-5, the tip electrode 38 and ring electrode 40 are each connected to a separate lead wire 30. Each lead wire 30 extends through the second off-axis lumen 28 in the tip section 14 (FIG. 5), through the central lumen 18 in the catheter body 12 (FIG. 3) and through the control handle 16. The proximal end of each lead wire 30 extends out the proximal end of the control handle 16 and is connected to an appropriate connector, which can be plugged into or otherwise connected to a suitable monitor, source of energy, etc.

The lead wires 30 are connected to the tip electrode 38 and ring electrode 40 by any conventional technique. Connection of a lead wire 30 to the tip electrode 38 is preferably accomplished by solder or the like. Connection of a lead wire 30 to the ring electrode 40 is preferably accomplished by first making a small hole through the tubing 24. Such a hole can be created, for example, by inserting a needle through the tubing 24 and heating the needle sufficiently to form a permanent hole. The lead wire 30 is then drawn through the hole by using a microhook or the like. The end of the lead wire 30 is then stripped of any coating and welded to the underside of the ring electrode 40, which is then slid into position over the hole and fixed in place with polyurethane glue or the like.

As also shown in FIGS. 2-5, two puller wires 32 extend through the catheter 10. Each puller wire 32 extends from the control handle 16, through the central lumen 18 in the catheter body 12 (FIG. 3) and into one of the off-axis lumens 26 and 28 of the tip section 14 (FIG. 5). As described in more detail below, proximal movement of the proximal end of each puller wire 32 is predeterminedly limited within the control handle 16 and the distal end of each puller wire 32 is anchored within the tip section 14.

Each puller wire 32 is made of any suitable metal, such as stainless steel or Nitinol. Preferably each puller wire 32 has a coating, such as a coating of Teflon® or the like. Each puller wire 32 has a diameter preferably ranging from about 0.006 inch to about 0.0010 inch. Preferably both of the puller wires 32 have the same diameter.

Each puller wire 32 is anchored near the distal end of the tip section 14. In the embodiment depicted in FIG. 4, the puller wires 32 are both anchored to the tip electrode 38 by a welding or the like.

Figure 7:
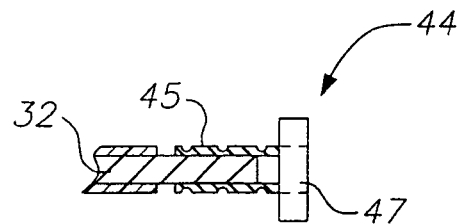
FIG. 7 is a longitudinal cross-sectional view of a preferred puller wire T-bar anchor.
Figure 8:
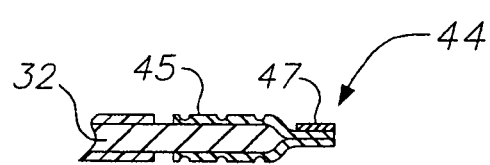
FIG. 8 is a longitudinal cross-sectional view of the puller wire T-bar anchor of FIG. 7 rotated 90.degree. to show the cross-piece on end.
Figure 9:
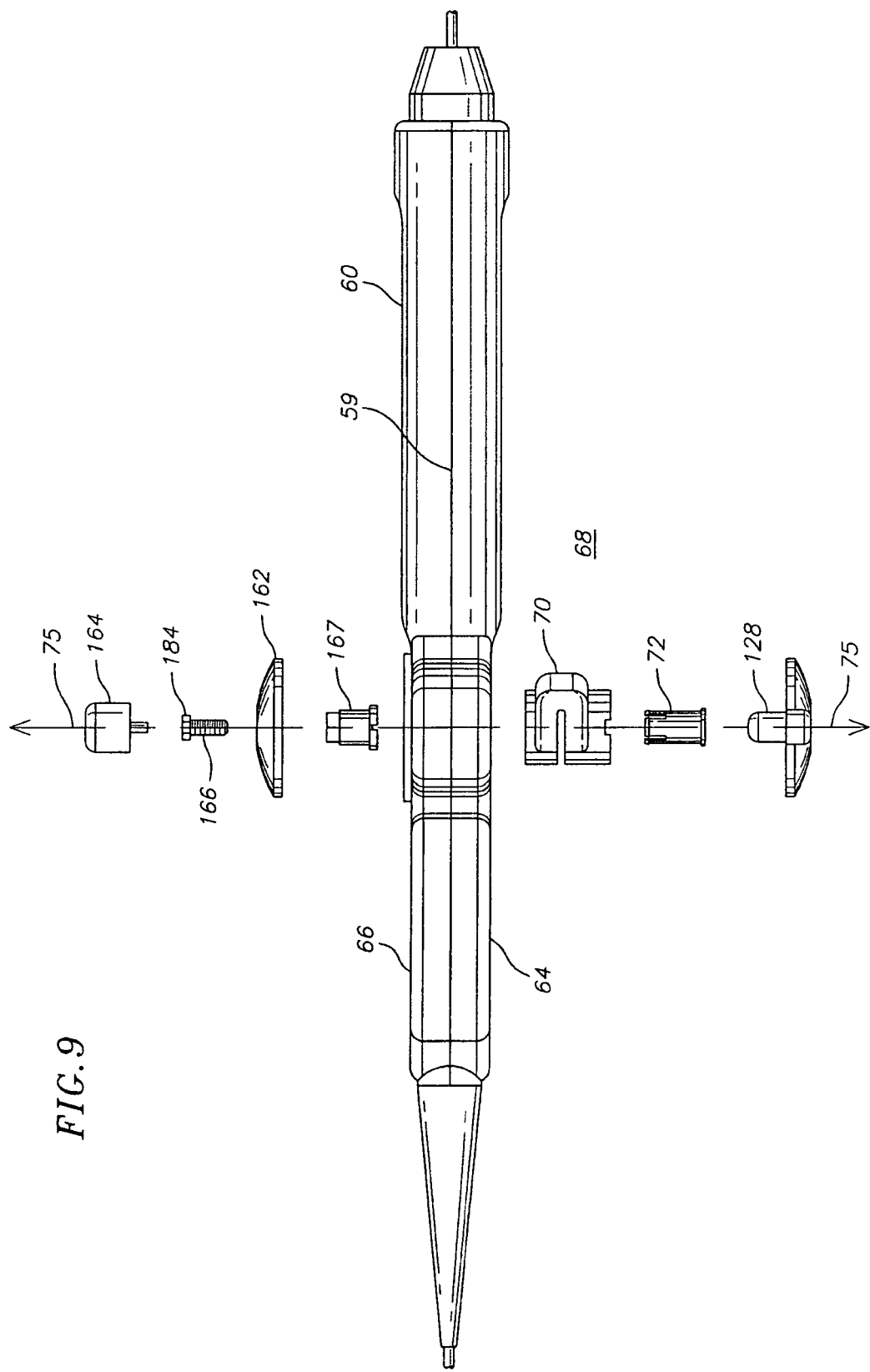
FIG. 9 is a top exploded view of a control handle of the catheter of FIG. 1.

Alternatively, the puller wire 32 in the first off-axis lumen 26 can be anchored to the side wall of the tip section 14. As shown in FIGS. 7 to 9, the puller wire 32 is preferably attached by means of an anchor 44 fixedly attached to the distal end of the puller wire 32. The anchor 44 is formed by a metal tube 45, e.g., a short segment of hypodermic stock, that is fixedly attached, e.g. by crimping, to the distal end of the puller wire 32. The tube has a section that extends a short distance beyond the distal end of the puller wire 32. A cross-piece 47 made of a small section of stainless steel ribbon or the like is soldered or welded in a transverse arrangement to the distal end of the metal tube which is flattened during the operation. This creates a T-bar anchor 44. A notch is created in the side of the tip section 14 resulting in an opening in the off-axis lumen 26 carrying the puller wire 32. The cross piece 47 lies transversely within the notch. Because the length of the ribbon forming the cross-piece 47 is longer than the diameter of the opening into the off-axis lumen 26, the anchor 44 cannot be pulled completely into the off-axis lumen 26. The notch is then sealed with polyurethane glue or the like to give a smooth outer surface. The glue flows into the off-axis lumen 26 to fully secure the anchor. A tunnel, in the form of polyimide tubing or the like, can be provided to permit passage of the lead wire 30 through the glue so that this same puller wire anchor construction can be used in the second off-axis lumen 28. Other means for anchoring the puller wires 32 in the tip section 14 would be recognized by those skilled in the art and are included within the scope of the invention.

Referring back to FIGS. 1 and 2, the catheter 10 further comprises two compression coils 46, each in surrounding relation to a corresponding puller wire 32. Each compression coil 46 is made of any suitable metal, such as stainless steel. Each compression coil 46 is tightly wound on itself to provide flexibility, i.e., bending, but to resist compression. The inner diameter of each compression coil 46 is slightly larger than the diameter of its associated puller wire 32. For example, when a puller wire 32 has a diameter of about 0.007 inch, the corresponding compression coil 46 preferably has an inner diameter of about 0.008 inch. The coating on the puller wires 32 allows them to slide freely within the compression coil 46. The outer surface of each compression coil 46 is covered along most of its length by a flexible, non-conductive sheath 48 to prevent contact between the compression coil 46 and the lead wires 30 within the central lumen 18. The non-conductive sheath 48 made of thin-walled polyimide tubing is presently preferred.

As shown in FIG. 2, at the distal end of the catheter body, the two compression coils 46 are positioned in diametric opposition within the stiffening tube 22 and spacer 36 so that they can be aligned with the two off-axis lumens 26,28 in the tip section 14. The compression coils 46 and stiffening tube 22 are sized so that the compression coils 46 fit closely and slidably within the stiffening tube 22. With this design, the lead wires 30 distribute themselves around the two compression coils 46 without misaligning the coils.

The compression coils 46 are secured within the catheter body 12 with polyurethane glue or the like. Each compression coil 46 is anchored at its proximal end to the proximal end of the stiffening tube 22 in the catheter body 12 by a glue joint (not shown). When a stiffening tube 22 is not used, each compression coil is anchored directly to the outer wall 20 of the catheter body 12.

Still referring to FIG. 2, the distal end of each compression coil 46 is anchored to the distal end of the stiffening tube 22 in the catheter body 12 by a glue joint 52, or directly to the distal end of the outer wall 20 of the catheter body 12 when no stiffening tube 22 is used. Alternatively, the distal ends of the compression coils 46 may extend into the off-axis lumens 26, 28 of the tip section 14 and are anchored at their distal ends to the proximal end of the tip section 14 by a glue joint. In the depicted embodiment, where the compression coils 46 are each surrounded by the sheath 48, care should be taken to insure that the sheath is reliably glued to the compression coil. The lead wires 30 can also be anchored in the glue joint. However, if desired, tunnels in the form of plastic tubing or the like can be provided around the lead wires at the glue joint to permit the lead wires to be slidable within the glue joint.

Both glue joints preferably comprise polyurethane glue or the like. The glue may be applied by means of a syringe or the like through a hole made between the outer surface of the catheter body 20 and the central lumen 18. Such a hole may be formed, for example, by a needle or the like that punctures the outer wall 18 and the stiffening tube 22 that is heated sufficiently to form a permanent hole. The glue is then introduced through the hole to the outer surface of the compression coil 46 and wicks around the outer circumference to form a glue joint about the entire circumference of each sheath 48 surrounding each compression coil 46. Care must be taken to insure that glue does not wick over the end of the coil so that the puller wire cannot slide within the coil.

As best shown in FIGS. 2 and 5, within the off-axis lumens 26, 28, each puller wire 32 is surrounded by a plastic sheath 42, preferably made of Teflon® The plastic sheaths 42 prevent the puller wires 32 from cutting into the wall of the tip section 14 when the tip section is deflected. Each sheath 42 ends near the distal end of each puller wire 32. Alternatively, each puller wire 32 can be surrounded by a compression coil where the turns are expanded longitudinally, relative to the compression coils extending through the catheter body, such that the surrounding compression coil is both bendable and compressible.

Longitudinal movement of the puller wires 32 relative to the catheter body 12, which results in deflection of the tip section 14, is accomplished by manipulation of the control handle 16. A suitable bidirectional control handle for use in the present invention is illustrated in FIGS. 9-24.

Figure 10:
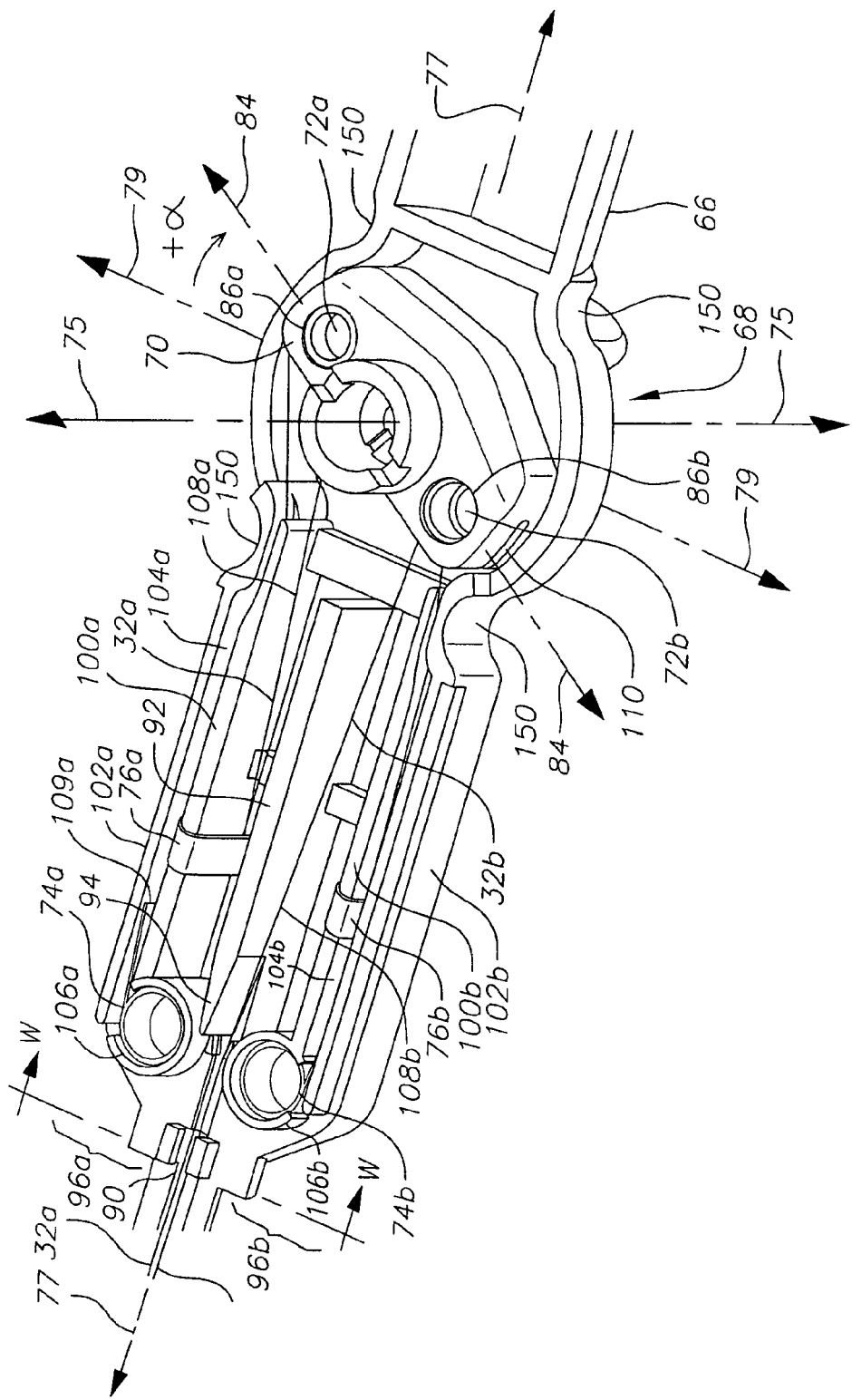
FIG. 10 is a view of a housing half of control handle and selected components of the steering assembly of the catheter of FIG. 1.

As shown in FIGS. 9 and 10, the control handle 16 comprises a generally elongated handle housing 60, which can be made of any suitable rigid material. The housing 60 can be of a unitary construction or of two opposing halves 64, 66 that are joined by glue, sonic welding or other suitable means along a longitudinal peripheral seam 59 around the housing. The control handle 16 comprises a steering assembly 68 that controls deflection of the tip section 14 in response to manipulations by the user. The steering assembly comprises a lever structure 70 having a pair of coordinated pulleys 72 that act on the puller wires to deflect the tip section, a pair of constant force springs 74 that are attached to the proximal ends of the puller wires, and a pair of adjustable stops 76 which prevent the proximal ends of the puller wires from moving proximally past a selected stop position within the control handle 16. The steering assembly 68 is advantageously configured to provide a relatively shorter angular throw while increasing, if not at least generally doubling, the throw capacity of the catheter. In particular, the steering assembly has a minimized moment of inertia about its throw axis 75, while generally doubling the travel distance of a puller wire in relation to the travel distance of the respective pulley drawing that puller wire, despite the relatively small interior of the housing. Moreover, the steering assembly provides a minimal angle between a longitudinal axis 77 of the control handle 16 and a segment of the puller wire drawn to accomplish deflection, for more efficient use of the force applied by the user in operating the control handle.

Figure 11A:
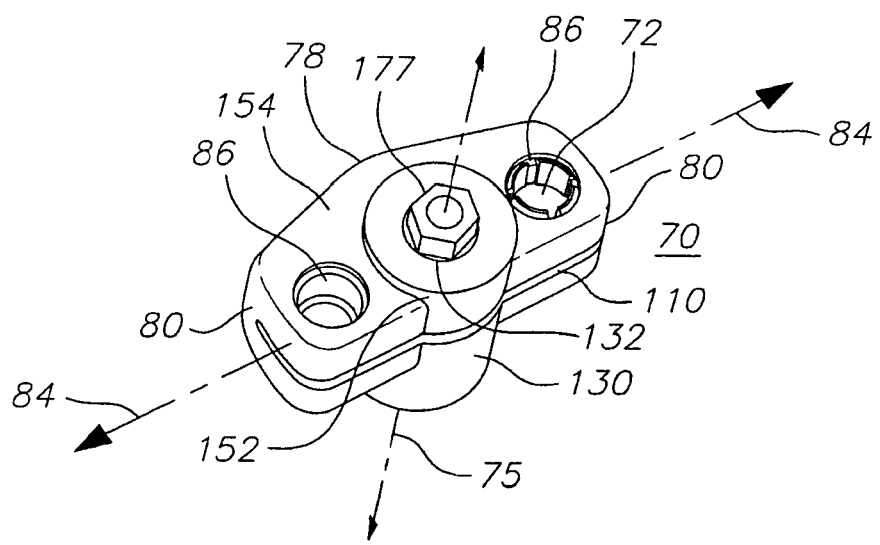
FIGS. 11a and 11b are views of a lever structure.
Figure 11B:
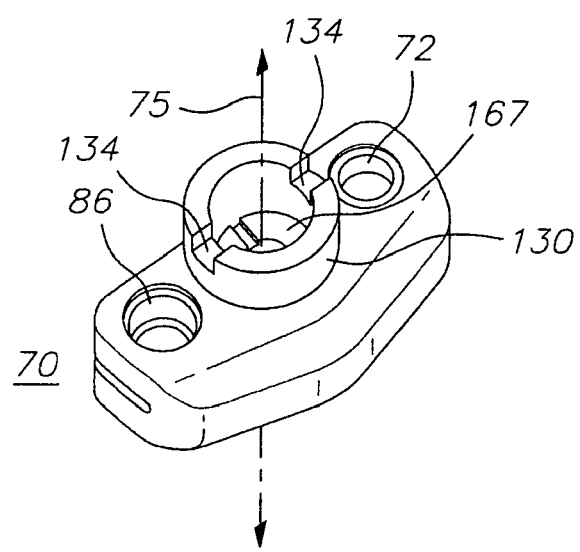
Figures 12A, 12B, 12C:
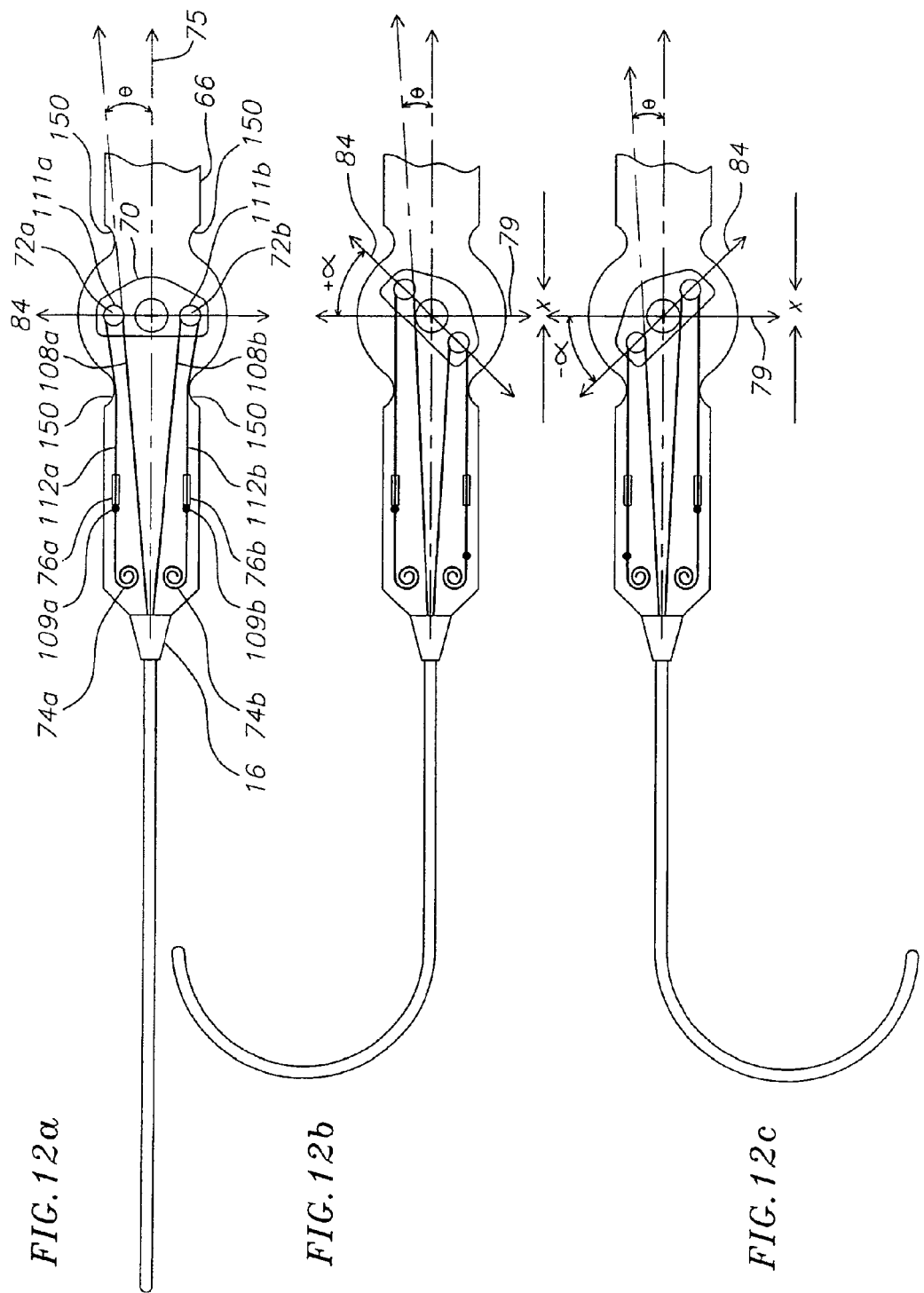
FIGS. 12a-12c show components of the steering assembly, respectively, as without deflection in the tip section of the catheter, with deflection of the tip section to the right, and with deflection of the tip section to the left.

As better shown in FIGS. 10, 11a and 11b, the lever structure 70 is somewhat elongated along an axis 84, having a wider center portion 78 between two narrower end portions 80. To deflect the tip section of the catheter, the lever structure is rotatable at its center about the throw axis 75, which is generally perpendicular to the longitudinal axis 77 of the control handle 16. A neutral position along axis 79 is defined for the lever structure when its longitudinal axis 84 is generally perpendicular to the longitudinal axis 77 of the control handle 16. The lever structure is rotatable from its neutral position in the clockwise direction by angle +α and in the counterclockwise direction by angle −α. The end portions 80 are configured with apertures 86, at a radial distance R from the throw axis 75, in which the pulleys 72 (of which only one is illustrated in FIGS. 10, 11a and 11b) are situated. As shown in FIGS. 12a-12c, with rotation of the lever structure 70, one pulley 72 is translated distally as the other pulley 72 is translated proximally. Moreover, the lever structure and the pulley are configured such that each pulley can rotate counterclockwise or clockwise within its aperture about its own axis. To that end, each pulley has a core 73 (FIG. 22) about which a puller wire is trained.

Referring more to FIG. 10, the housing 60 is configured at its distal end with a port 90 through which the puller wires (now designated as 32a and 32b for more clarify) enter the control handle 16. In the housing half 66 that is shown in FIG. 10, a divider 92 is configured in the inner surface and proximal of the port to extend linearly between the port and the lever structure 70. A distal end 94 of the divider is tapered to define diverging puller wire pathways from the port toward a respective pulley 72 in the lever structure. For ease of discussion, the housing half 66 may be described as divisible along the divider 92 into top and bottom housing quarters 96a, 96b, which are more or less mirror counterparts of each other in terms of physical layout and operation. Accordingly, the following description uses similar reference numerals for similar structures except the numerals are followed by the letter a or the letter b.

The top housing quarter 96a is configured with a rail 100a that extends parallel with the divider 92. The rail and an adjacent side 102a of the housing 60 define a channel 104a that extends between the pulley 72a and the distal end of the housing quarter which is configured with a well 106a that is in communication with the channel. Fixedly situated in the well is the spring 74a whose free end 109a extends proximally into the channel. Releasably and hence adjustably mounted onto the rail 100a is the stop 76a.

Correspondingly, the bottom housing quarter 96b is configured with a rail 100b that extends parallel with the divider 92. The rail and an adjacent side 102b of the housing define a channel 104b that extends between the pulley 72b (not shown) and the distal end of the housing quarter which is configured with a well 106b that is in communication with the channel. Fixedly situated in the well is the spring 74b whose active end 109b extends proximally into the channel. Releasably and hence adjustably mounted onto the rail 100b is the stop 76b.

The inner surface of the housing half 64 has formations in structural correspondence with the aforementioned formations of the housing half 66. Accordingly, as shown in FIG. 23, the inner surface is formed with a counterpart divider 93, counterpart rails 101, counterpart sides 103, and counterpart wells 107.

In view of the foregoing, the travel path within the housing of each puller wires is as follows: a first generally linear path, a non-linear (including, e.g., a U-turn or doubling back) path, and a second generally linear path, each leg of which is described below in further detail.

Referring to FIGS. 10 and 12a, the puller wire 32a, whose distal end is affixed to the tip section 14, enter the control handle 16 in a proximal direction via the port 90. At the tapered distal end 94 of the divider 92, the puller wire 32a diverges from the puller wire 32b and continues proximally in a minimally diagonal direction toward the pulley 72a in the lever structure 70. This section of the travel path, as defined between the tapered end 94 and the pulley 72a, is generally linear. This linear segment of the puller wire 32a is hereinafter generally referred to by the numeral 108a (FIG. 12a).

The puller wire 32a then enters the lever structure 70 proximally through a slit opening 110 (best seen in FIG. 11a) on the distal side of the lever structure and is trained counterclockwise about the pulley 72a before exiting the lever structure distally through the same slit opening. The puller wire is trained about the pulley for a predetermined degree ranging between about 172-195, preferably 177-190, or more preferably about 180-187. As such, the travel path of the puller wire 32 also includes a section having a U-turn or a doubling-back at the pulley. This nonlinear segment of the puller wire is designated by the numeral 111a (FIG. 12a).

The puller wire 32a then veers inwardly and continues generally distally to enter the channel 104, which defines yet another section of the travel path. Within the channel, the proximal end of the puller wire (so designated despite its being physically distal of a preceding segment) is attached to the free end 109a of the spring 74a. The linear segment of this travel path is designated by the numeral 112a (FIG. 12a).

Correspondingly, the puller wire 32b travels a similar path having a first linear segment 108b, followed by a nonlinear segment 111b and further followed by a second linear segment 112b, except that the segment 111b is trained clockwise on the pulley 72b. Moreover, the proximal end of the puller wire 32b (so designated despite its being physically distal of a preceding segment) is attached to the free end 109b of the spring 74b (not visible in FIG. 10).

In the disclosed embodiment, the constant force springs 74a, 74b are flat coil springs as best seen in FIG. 10. Each spring member exerts a force in the distal direction ranging between about 0.50 ounces and 9.0 ounces, and preferably of about 1.0 ounce. As shown in FIGS. 13a and 13b, free ends 109a, 109b of the springs 74a, 74b are attached to the proximal ends of the puller wires 32a, 32b by a fastener 111, e.g., a crimp fastener 113 (FIG. 13a), a welded joint 114 (FIG. 13b).

Configured to act on the free ends 109 are the stops 76 which limit extension of the ends 109 in the proximal direction (and hence proximal movement of the proximal ends of the puller wires 32) past a predetermined stop location along the rails 100. Accordingly, each stop 76a, 76b is positioned proximally of the respective free end 109 and/or fastener 111. As shown in FIGS. 14a and 14b, each stop can comprise a generally U-shaped spring clip member 76i (e.g., constructed from a shaped piece of sheet metal) having a base 116 and legs 118 that releasably straddle the rail. The member 76i is shaped such that one of its legs 118 sits deep in the channel 104 and projects minimally into the channel so as to avoid interfering with the distal or proximal movement of the puller wires 32 but sufficiently to stop the free ends 109 of the springs or the fastener 111 from passing proximally.

As shown in FIGS. 14c-14d, each stop can also comprise a generally S-shaped spring clip member 76j (e.g., constructed from a piece of shaped sheet metal) which has a first arm 117 that wraps around either the rail 100 or the side 102 and a second arm 119 that sits deep in the channel 104 to adjustably anchor the member 76j to the rail 100, the side 102 and/or in the channel 104. Again, the member 76j has a profile that projects minimally into the channel 104, but sufficiently so as to block the free ends 109 of the springs 74 or the puller wire fastening means from passing proximally.

Each stop can further comprise a hollow elongated member 76k (e.g., a cylinder formed from a rolled piece of sheet metal) whose an interior space or volume along the length is generally constant until at its proximal end 121 which can flare when the circumference is unrestrained. A corresponding, thus close-fitting tubular cross section 123 is provided in facing surfaces of the rail 100 and the side 102 such that the member 76k can slide or move distally within the channel 104 but is generally restricted against proximal movement by the frictional engagement of the flared proximal end 121 against the rail and the wall within the cross section 123. It is understood that the configuration or form of the stops 76a, 76b is limited by only its function and purpose to adjustable set a stop position and the stops may therefore take on other forms not expressly described herein.

It can be seen from FIGS. 12a-12c. that rotation of the lever structure 70 causes deflection in the catheter tip section 14. That is, when the lever structure is rotated in the clockwise rotation (namely, in the +α direction) (FIG. 12b), the pulley 72a is translated proximally. Because the puller wire 32a trained on the pulley 72a is stopped against proximal movement at its proximal end by the stop 76a, the proximal translation of the pulley 72a causes it to rotate counterclockwise thereby drawing proximally the wire segment 108a, which results in deflection of the tip section 14 to the right. Facilitating this deflection is the release of the segment 112b as the pulley 72b is coincidentally translated distally by the lever structure 70. The resulting slack in the segment 112b is taken up by the spring 74b as the pulley 72b rotates clockwise.

Correspondingly, when the lever structure is rotated in the counterclockwise rotation (namely, in the −α direction) (FIG. 12c), the pulley 72b is translated proximally. Because the puller wire 32b trained on the pulley 72b is stopped against proximal movement at its proximal end by the stop 76b, the proximal translation of the pulley 72b causes it to rotate clockwise thereby drawing proximally the wire segment 112b, which results in deflection of the tip section 14 to the left. Facilitating this deflection is the release of the segment 112a as the pulley 72a is coincidentally translated distally by the lever structure 70. The resulting slack in the segment 112a is taken up by the spring 74a as the pulley 72a rotates counterclockwise.

Although each of the actuating pulley has translated proximally only a distance x (FIGS. 12b and 12c) along the longitudinal axis 75 as a result of the rotation of the lever structure 70, the length of the puller wire drawn by that pulley proximally from the port in deflecting the tip section is about 2×. Consequently, the present invention provides a catheter with nearly double the throw in tip deflection, despite the small interior space of the control handle.

Because of the repeated cycles of bending each puller wire can experience around its pulley, the proximal segment(s) of each puller within the control handle may comprise a flexible braided cable and/or Kevlar® rope which can better withstand such stress and strain. To that end, the cable or rope has a length of at least 2×, with a portion thereof trained around the pulley. Its distal and proximal ends may be attached to the puller wire and the spring, respectively, by crimp fasteners. Accordingly, it is understood that the proximal end of the puller wire and the proximal end of the cable or rope are used interchangeably herein as appropriate.

Also in accordance with the present invention, as shown in FIGS. 12a-12c, an angle of alignment of the segments 108a, 108b deviates only minimally from the longitudinal axis 77 which provides greater operating efficiency in the force required to deflection the tip section 14. In the disclosed embodiment, a deviation angle θ may range between about 5 to 12 degrees, preferably between 6 and 10 degrees and more preferably between 7 and 8 degrees, when the lever structure is in the neutral position (namely, when α is at or near 0) (FIG. 12a). Because the pulleys 72 each travel a circular path when translated by the lever structure 70, the angle θ can be further decreased by up to about 2-4 degrees (that is, decreases down to about θ=3) during this translation (FIGS. 12b and 12c). In any case, given such a minimal range of angle θ, most of the force that is applied to draw a puller wire proximally along the longitudinal axis 77 for deflecting the tip section in the direction of the off axis lumen in which that puller wire extends is advantageously met by the proximal translation of the pulley drawing that puller wire along the angle θ.

In accordance with the present invention, an initial neutral position (with little or no detectable deflection) (FIG. 12a) in the tip section 14 can be readily calibrated by selective placement of each of the stops 76a, 76b distally or proximally along the rails 100a, 100b. With the lever structure 70 resting in a neutral position, the operating position of each puller wire 32 can be adjusted so that it is sufficiently taut in drawing the ends 109 of the springs 74 against the stops 76 without causing any detectable deflection in the tip section 14. As described above in relation to FIGS. 11-13, the stop location of each stop 76a, 76b determines how much distance the corresponding pulley needs to be moved (or the corresponding puller wire needs to travel) proximally before the tip section 14 begins to deflect in that direction. In that regard, it is understood that the puller wires can also be adjusted to provide the catheter with a predetermined amount of free play in the neutral position so that the catheter body and/or elements surrounding the puller wires (e.g., the outer wall 20 and/or the stiffening tube 22) can shrink or stretch, such as during sterilization of the catheter, without adversely deforming the puller wires. In accordance with the present invention, fine, if not near infinitesimal, adjustment of a stop position for each puller wire is enabled in the control handle 16. As such, these adjustments of the stop position of each puller wire can also be used to compensate for certain characteristics in the catheter, including puller wires with unequal actual lengths and/or counterpart components in the steering assembly or the control handle that are not exact duplicates of each other in terms of size or operating characteristics. Stop adjustments should be performed to attain a neutral position with little or no detectable deflection in the catheter tip section 14 before the housing halves 64, 66 are joined to each other.

Referring back to FIG. 9, the lever structure 70 of the steering assembly 68 is enclosed within the housing halves 64, 66 and is manipulated from outside the housing by a deflection knob 128. Deflection of the catheter 10 can therefore be comfortably controlled by, preferably, the thumb and/or index finger of the user when grasping the control handle 16. Rotation of the deflection knob about the throw axis 75 is directly coupled to rotation of the lever structure 70 primarily by means of an annular protrusion 130 (FIGS. 10 and 11b) formed in the lever structure. The protrusion 130 is centered about an aperture 132 aligned with the throw axis 75 and extends in the direction of the deflection knob 128. The protrusion 130 has two recesses 134 aligned along a diameter which allows the lever structure to lock in alignment with the deflection knob. The protrusion also has a dimension along the throw axis 75 that enables the protrusion to extend through and beyond an aperture 136 in the housing half 64 (FIG. 23) to reach a facing surface 138 of the deflection knob 128 (FIG. 15). The facing surface 138 is formed with counterpart annular recess 140 and similarly aligned protrusions 142 that match, respectively, the annular protrusion 130 and aligned recesses 134 of the lever structure 70. These matching formations are sized such that the deflection knob can be frictionally or snap-fitted (and secure by glue if appropriate) through the aperture 136 the housing half 64 onto the protrusion 130 of the lever structure. In this manner, the deflection knob 128 and the lever structure 70 are joined to the housing half 64 yet coupled for joint rotation relative to the housing half 64 about the throw axis 75. Consequently, clockwise rotation of the deflection knob causes clockwise rotation of the lever structure, and counter-clockwise rotation of the deflection knob causes counterclockwise rotation of the lever structure. In the disclosed embodiment, the recesses 134, 140 and protrusions 130, 142 are also conveniently aligned with arms 144 (FIG. 15) of the deflection knob so as to give the user a visual indication of the rotational position or orientation of the lever structure 70.

Because the deflection knob 128 and the lever structure 70 are rotational coupled, rotation of the deflection knob may also be described in terms of the aforementioned angle α. As illustrated in FIGS. 12a-12c, the range of angle α is predetermined primarily by the arcuate profile of the housing near the throw axis 75. Concave or generally recessed sections 150 (see also FIG. 10) of the housing halves 64, 66 abut with the arms 144 of the deflection knob thus preventing further clockwise rotation beyond the angle +α (FIG. 12b) and counterclockwise rotation beyond the angle −α (FIG. 12c). It is understood that the range of rotation of the deflection knob 128 can be varied by altering the profile or curvature of the sections 150. Moreover, the sections 150 on each side of the neutral position of the lever structure 70 need not be identical; a greater counterclockwise rotation angle and/or a lesser clockwise rotation angle are possible, and vice versa.

In the disclosed embodiment, the angle α of the lever structure 70 (and hence the deflection knob 128) ranges between about 0 and 70 degrees, preferably between about 30 and 60 degrees and more preferably between about 40 to 50 degrees. Accordingly, the disclosed embodiment provides a total range of rotation (from −α to +α) of between about 0 and 140 degrees, preferably between about 60 and 120 degrees and more preferably between about 80 to 100 degrees.

Significantly, the control handle 16 is configured such that it need not be fully assembled for the steering assembly 68 and deflection of the tip section 14 to be effectively tested and evaluated. In particular, the steering assembly 68 can be tested and evaluated when assembled solely within the housing half 66 and operated on by the deflection knob 128 mounted onto the lever structure without the housing half 64. To that end, the housing half 66 is configured at or near the port 90 with a formation 91 (FIG. 24) that releasably holds the proximal end of the catheter body 12 (whose outer wall 20 and stiffening tube 22 generally terminate proximal of the formation 91 so that the pulley wires 32 and can extend freely and uncovered into the control handle 16). The formation can include a pair of tabs 93 defining a space in which the catheter body can be snapped into and releasably held to facilitate the testing and evaluation of the deflection operation of control handle without the housing half 64.

In the assembly of the remainder of the control handle, reference is made to FIGS. 9, 11a, and 16-21. A second annular protrusion 152 on a surface 154 of the lever structure 70 facing the housing half 66 is received in an annular indentation 156 (FIG. 19) formed in the housing half 66. The annular indentation 156 of the housing half 66 is concentric with an aperture 158 that is aligned with the throw axis 75 and has a geometric (non-circular) or hexagonal cross-section. In the illustrated embodiment, the control handle 16 includes a tension adjustment mechanism 160 (FIG. 9) that is mounted onto the outside of the housing half 66. The mechanism 160 which can be manipulated to adjust the tightness or tension of the rotational movement of deflection knob 128 includes a cap 162 and a finger dial 164 that are rotationally coupled, a friction screw 166 that is rotationally coupled to the cap, and a friction nut 167 that is in engagement with the friction screw 166.

Figure 17:
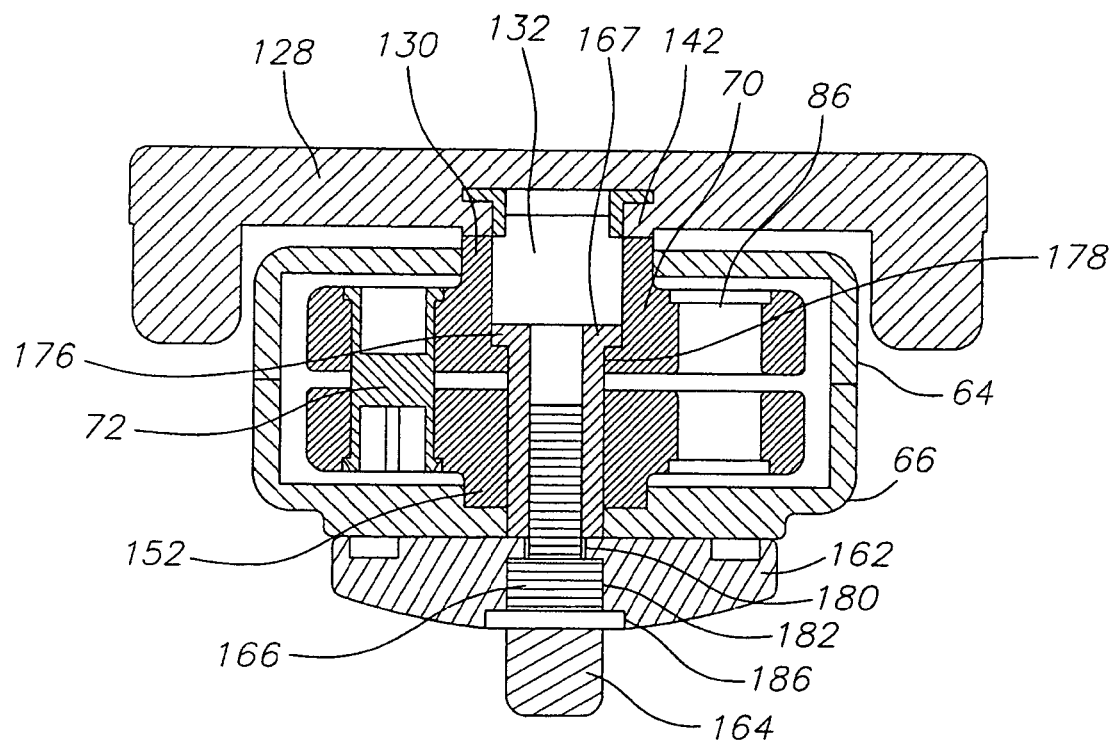
FIG. 17. is a cross-sectional view of the control handle of the catheter of FIG. 9 taken generally along the axis 75 parts broken away.
Figure 18:
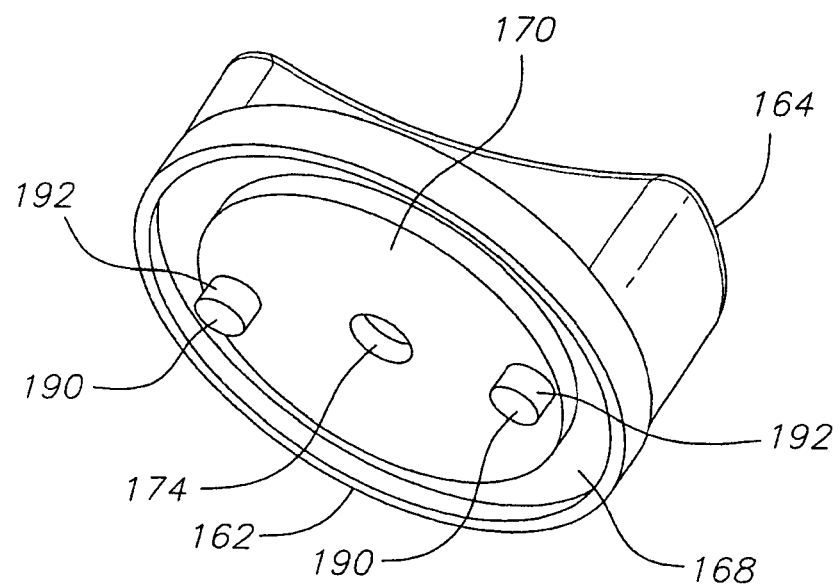
FIG. 18. is a view of components of a tension adjustment assembly.

As best shown in FIG. 17, the friction nut 167 is situated in the aperture 132 of the lever structure 70. The friction nut is configured with a lip 176 at one end that engages with a corresponding diameter 178 in the aperture 132 of the lever structure 70. The lip 176 and the diameter 178 are oriented such that they point toward the deflection knob 128. On an end face of the lip, there are two recesses on a diameter of the outer surface of the lip 179 which can receive the head of a screwdriver that may be used during assembly of the control handle 16. At an end 169 of the nut 167, it is provided with a geometric or hexagonal cross section 177 that matches the aperture 158 of the housing half 66. The length of the nut 167 allows the end 169 to be received in the aperture 158 so that the nut is secured with the housing half 66 against rotation about the throw axis 75.

An inner surface 168 of the cap 162 (FIG. 18) facing the outside of the housing half 66 defines a raised circular portion 170 that fits within a corresponding indented circular portion 172 (FIG. 19) in the outer face of the housing half 64. With a central aperture 174 (FIG. 18) of the cap concentric with the hexagonal aperture 158 (FIG. 19) which leads to a threaded interior of the friction nut 167 (FIG. 17) within the lever structure 70, the screw 166 (not shown in FIG. 17, but shown in FIG. 9) is inserted through the aperture 174 and the aperture 158 and its end advanced into threaded engagement with the end 169 of the friction nut 167. As shown in FIG. 20, the aperture 174 has three depths when viewed from its outside surface. A first depth has a smaller circular cross section 180 defining a passage for the screw 166 completely through the cap 162. A second depth has a geometric or hexagonal cross section 182 about mid-depth so as to anchor a geometric or hexagonal screw head 184 (FIG. 9) against axial movement toward the friction nut 167 and to rotationally couple the cap 162 and the screw 166 to each other. A third depth 186 has a larger circular cross section whose depth sufficiently enables the cap to receive a facing circular portion 188 of the finger dial 164 (FIG. 22).

Figure 19:
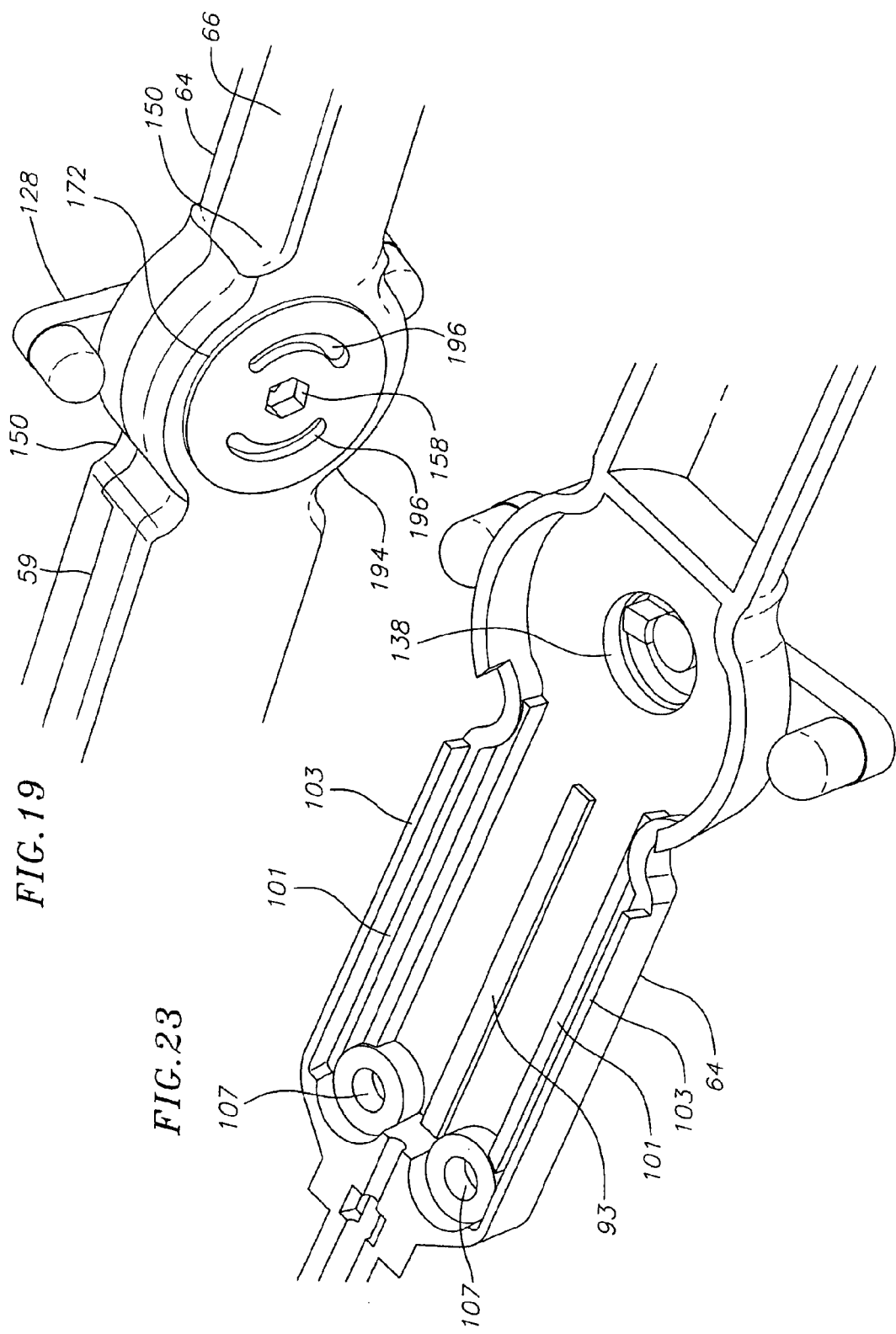
FIG. 19 is a view of a first housing half joined with a second housing half.

Referring to FIGS. 19-21, covering the screw head 184, the finger dial 164 is mounted outside of the cap 162 by prongs 190 (FIG. 21) that protrude from the finger dial in opposing positions across the portion 188, for frictional snug fitting into (and beyond) apertures 192 (FIGS. 18, 20) form on a diameter of the cap 162. And, because the cap 162 and the finger dial 164 have rotational freedom relative to the housing half 66, the outside surface 194 of the housing half 66 is configured with two curved recesses 196 (FIG. 19) which not only accommodate rotation movement of the ends of the prongs 190 extending past the cap, but effectively limit such rotational movement about the throw axis 75 to about 60 degrees, preferably about 50 degrees, or more preferably about 45 degrees. Accordingly, when the finger dial 164 is rotated, the cap 162 (rotationally coupled thereto by the prongs 190) and the screw 166 (rotationally coupled to the cap 162 by the hexagonal head 184) are jointly rotated.

Where the dial 167 is rotated to advance the screw 166 into the friction nut, the friction nut 167 is drawn toward the adjustment mechanism 160 thereby drawing the lever structure 70 toward the inside of the housing half 66 to increase the frictional contact or bearing between the second annular protrusion 152 of the lever structure 70 against the indented circular portion 172 of the inner surface of housing half 66. The tension of the lever structure 70 and hence the deflection knob 128 against rotational movement is thereby increased. Correspondingly, where the dial 164 is rotated to draw the screw 166 out of the friction nut 167, the bearing of the protrusion 152 of the lever structure 70 against the portion 172 of the housing half 66 is decreased thereby decreasing the tension of the lever structure 70 and the deflection knob 128 against rotation. This bearing between the lever structure 70 and the housing half 66, which can affect whether the deflection knob is at all rotatable, how much force the user is to apply in deflecting the tip section and whether and/or how quickly the tip section can straighten after deflection when the deflection knob is released, can therefore be tightened or loosen as desired by the user in operating the deflection knob 128.

In other embodiments, one or more additional off axis lumens may be provided through which additional components, e.g., infusion tube, optic fiber, etc., may extend. Depending on the intended use of the catheter 10, it can further comprise additional features such as temperature sensing means, an optic fiber, an infusion tube, and/or an electromagnetic sensor. Additionally, smaller components, such as a temperature sensing means, could also extend through the second lumen in the tip section along with the puller wire and lead wire(s).

In the embodiments described above, the central lumen 18 of the catheter body 12 is used for passage of the electrode lead wires 30 as well as the two puller wires 32, compression coils 46 and, if present, thermocouple wires, electromagnetic sensor cable, optic fiber or infusion tube. It is understood that the catheter body 12 could alternatively comprise a plurality of lumens. However, the single central lumen 18 is preferred because it has been found that a single lumen body permits better control when rotating the catheter 10. The single central lumen 18 permits the puller wires 32, compression coils 46 and lead wires 30 to float freely within the catheter body 12. If such wires are restricted within multiple lumens, they tend to build up energy when the control handle 16 is rotated, resulting in the catheter body 12 having a tendency to rotate back if, for example, the handle 16 is released, or if bent around a curve, to flip over, either of which are undesirable performance characteristics.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:
1. A bi-directional catheter comprising:
   an elongated catheter body having proximal and distal ends;
   a catheter tip section at the distal end of the catheter body and comprising first and second diametrically-opposed off-axis lumens;
   a control handle at the proximal end of the catheter body, the control handle housing a steering assembly, the steering assembly comprising a lever structure rotatable about a throw axis substantially perpendicular to a longitudinal axis of the control handle, the lever structure comprising:
      a center portion through which the throw axis extends,
      a first end portion comprising a first aperture positioned at a first radial distance from the throw axis,
      a first pulley situated in the first aperture,
      a second end portion comprising a second aperture positioned at a second radial distance from the throw axis, and
      a second pulley situated in the second aperture; and
   first and second puller wires configured to deflect the tip section in response to the steering assembly, the first puller wire being trained on the first pulley and extending into the first off-axis lumen in the tip section, and the second puller wire being trained on the second pulley and extending into the second off-axis lumen in the tip section;
   wherein rotation of the lever structure in a first direction results in proximal movement of the first pulley relative to the control handle thereby drawing proximally at least a segment of the first puller wire resulting in deflection of the tip section in the direction of the first off-axis lumen, and rotation of the lever structure in a second direction opposite the first direction results in proximal movement of the second pulley relative to the control handle thereby drawing proximally at least a segment of the second puller wire resulting in deflection of the tip section in the direction of the second off-axis lumen.

2. A bi-directional catheter of claim 1, wherein each of the puller wires is trained about its respective pulley for at least about 180 degrees.

3. A bi-directional catheter of claim 1, wherein each puller wire extends from a distal end of the control handle to its respective pulley at an angle of no greater than about 10 degrees from the longitudinal axis of the control handle.

4. A bi-directional catheter of claim 1, wherein each puller wire extends from a distal end of the control handle to its respective pulley at an angle ranging between about 3 and 10 degrees from the longitudinal axis of the control handle.

5. A bi-directional catheter of claim 1, wherein the control handle further comprises a deflection knob, wherein the deflection knob and the lever structure are rotationally coupled to each other.

6. A bi-directional catheter of claim 5, further comprising an adjustment knob configured to adjust tension of the deflection knob.

7. A bi-directional catheter of claim 6, wherein the adjustment knob comprises a dial and a member configured to draw the lever structure toward a housing of the control handle in response to rotation of the dial.

8. A bi-directional catheter of claim 1, further comprising:
   first and second constant force springs;
   a first stop positioned proximal a first connection between the first constant force spring and a proximal end of the first puller wire;
   a second stop positioned proximal a second connection between the second constant force spring and a proximal end of the second puller wire.

9. A bi-directional catheter of claim 8, wherein the first and second stops prevent the proximal ends of the first and second puller wires from moving proximally beyond respective threshold locations along the longitudinal axis of the control handle.

10. A bi-directional catheter of claim 1, wherein the constant force springs are positioned distal of the pulleys.

11. A bi-directional catheter of claim 1, further comprising a divider extending along the longitudinal axis of the control handle, said divider directing each of the puller wires at a threshold angle toward its respective pulley.

12. A bi-directional catheter of claim 1, wherein the lever structure rotates within a threshold range of angles from the throw axis.

13. A bi-directional catheter of claim 12, wherein the threshold range of angles is about −50 to +50 degrees.

14. A bi-directional catheter of claim 1, wherein the first pulley is rotatable within the first aperture, and the second pulley is rotatable within the second aperture.

15. A bi-directional catheter of claim 14, wherein the first pulley comprises a first pulley core about which the first puller wire is trained, and the second pulley comprises a second pulley core about which the second puller wire is trained.

16. A bi-directional catheter of claim 1, further comprising a tip electrode at a distal end of the tip section.

17. A bi-directional catheter of claim 16, wherein distal ends of the first and second puller wires are anchored to the tip electrode.

18. A bi-directional catheter of claim 1, wherein a proximal end of the first puller wire is connected to a first constant force spring, and a proximal end of the second puller wire is connected to a second constant force spring.

19. A bi-directional catheter of claim 1, further comprising:
   a first stop positioned proximal the lever structure and configured to limit proximal movement of a proximal end of the first puller wire;
   a second stop proximal the lever structure and configured to limit proximal movement of a proximal end of the second puller wire.

20. A bi-directional catheter of claim 1, wherein the lever structure further comprises a slit opening through which the first and second puller wires enter and exit the lever structure.

\* \* \* \* \*